(12) United States Patent
Ishitani et al.

(10) Patent No.: US 6,348,488 B1
(45) Date of Patent: Feb. 19, 2002

(54) REMEDIES FOR MOTOR DYSFUNCTION AND GAPDH EXPRESSION INHIBITORS

(75) Inventors: Ryoichi Ishitani, Shiki; Nobuo Katsube, Mishima-gun, both of (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/806,572

(22) PCT Filed: Oct. 1, 1999

(86) PCT No.: PCT/JP99/05414

§ 371 Date: Apr. 2, 2001

§ 102(e) Date: Apr. 2, 2001

(87) PCT Pub. No.: WO00/20387

PCT Pub. Date: Apr. 13, 2000

(30) Foreign Application Priority Data

Oct. 2, 1998 (JP) ............................ 10-281498

(51) Int. Cl.$^7$ .............................................. A61K 31/40
(52) U.S. Cl. ....................................... 514/422
(58) Field of Search ......................... 514/422

(56) References Cited

U.S. PATENT DOCUMENTS 4,956,380 A    9/1990    Toda et al.

FOREIGN PATENT DOCUMENTS

JP                 235162            8/1992

OTHER PUBLICATIONS

International Search Report dated Dec. 14, 1999 for PCT/JP99/05414.

*Primary Examiner*—Raymond Henley, III
(74) *Attorney, Agent, or Firm*—Stevens, Davis, Miller & Mosher, L.L.

(57) ABSTRACT

Remedies for motor dysfunction and GAPDH expression inhibitors containing as the active ingredient N-[3-[N-(4-chlorophenylmethyl)carbamoyl]propanoyl]-L-prolinal. Since it has an effect of ameliorating motor dysfunction, N-[3-[N-(4-chlorophenylmethyl)carbamoyl]propanoyl]-L-prolinal is useful in treating motor dysfunction caused by trauma, infection, degeneration, ischemia, tumor, etc. Also, it is useful in treating diseases caused by apoptosis in the cerebellum, spinal nerve nucleus or conduction route due to the overexpression of GAPDH (Parkinson's diseases, Parkinson's syndrome, Huntington's disease, MJD, ALS, CHJ diseases, etc.).

12 Claims, 5 Drawing Sheets

REMEDIES FOR MOTOR DYSFUNCTION AND GAPDH EXPRESSION INHIBITORS

This is a 371 of PCT/JP99/05414 filed Oct. 1, 1999.

TECHNICAL FIELD

The present invention relates to:

1) A remedy for motor dysfunction, comprising as an active ingredient N-[3-[N-(4-chlorophenylmethyl) carbamoyl]propanoyl]-L-prolinal,
2) A remedy for a disease caused by overexpression of glyceraldehyde-3-phosphate dehydrogenase (hereinafter, abbreviated as "GAPDH"), comprising the same compound as above as an active ingredient, and
3) An inhibitor for apoptosis containing the same compound as above as an active ingredient.

BACKGROUND ART

Prolyl endopeptidase (post-proline cleaving enzyme; abbreviated as "PPCE") is an enzyme that hydrolyzes many proline-containing peptide hormones to inactivate them. Examples of proline-containing peptide hormones include vasopressin, oxytocin, substance P, neurotensin, bradykinin, angiotensin II, thyroid gland stimulating hormone release factor (TRH), etc. Among these neuropeptides, particularly vasopressin relates to memory and learning. Therefore, its inhibition of the enzyme is considered to be useful for the therapy of cognition failure, so that N-[3-[N-(4-chlorophenylmethyl)carbamoyl]propanoyl]-L-prolinal has been developed as an anti-dementia drug.

N-[3-[N-(4-chlorophenylmethyl)carbamoyl]propanoyl]-L-prolinal is the compound described in Example 2(f) of Japanese Patent Publication 6-4583 (European Patent No. 2681190). Japanese Patent Publication 6-4583 describes that proline derivatives inclusive of this compound inhibit PPCE and hence they are useful in the prevention and/or therapy of amnesia.

Previously, the present inventors have reported that rat cerebellar granule cells (CGC) when subcultured in the presence of KCl (25 mM) without exchanging with fresh culture medium or supplementing glucose caused apoptosis suddenly after 2 weeks or more from the initiation of the culture (Japanese Patent Application Laid-open No. 8-92127).

Since it is inhibited by N-methyl-D-aspartate (NMDA) receptor antagonist and antioxidants, the age-induced apoptosis of CGC is considered to be attributable to overstimulation of NMDA receptor by glutamic acid that is released endogenously or to subsequently formed activated oxygen species.

Further, it has also been elucidated that overexpression of glyceraldehydes-3-phosphate dehydrogenase (GAPDH) (a typical glycolytic enzyme that has many non-glycolytic functions) is closely connected with the age-induced apoptosis of CGC.

Inhibition of mRNA of GAPDH with GAPDH anti-sense oligonucleotide results in inhibition of the overexpression of proteins, which in turn inhibits age-induced apoptosis of neuronal cells. Therefore, inhibition of expression of GAPDH mRNA or GAPDH protein enables inhibition of apoptosis.

GAPDH is also known to selectively bind to gene products (particularly triplet repeat proteins) that are causative proteins in other neurodegenerative diseases (Burke et al., 1996; Koshy et al., 1996). The gene products include huntingtin in Huntington's disease, atrophin in dentate nucleus red nucleus pale globe Luys' body atrophy (DRPLA), ataxin in inherited spine cerebellum degeneration (SCA-1), ataxin-3 in Machado-Joseph's disease, androgen receptor in spino-bulbar muscular atrophy (SBMA), etc. Accordingly, it is considered that GAPDH would play some role in these diseases.

DISCLOSURE OF THE INVENTION

The present invention relates to:

1) A remedy for motor dysfunction, comprising as an active ingredient N-[3-[N-(4-chlorophenylmethyl) carbamoyl]propanoyl]-L-prolinal,
2) A remedy for a disease caused by the overexpression of GAPDH, comprising the same compound as above as an active ingredient, and
3) An inhibitor for apoptosis comprising the same compound as above as an active ingredient.

The present inventors have found that N-[3-[N-(4-chlorophenylmethyl)carbamoyl]propanoyl]-L-prolinal hitherto known as a PPCE inhibitor is effective to motor dysfunction model of a neuropathic type and improves the disorder significantly, thus having completed the present invention.

Also, the present inventors have additionally found that N-[3-[N-(4-chlorophenylmethyl)carbamoyl]propanoyl]-L-prolinal inhibits the overexpression of GAPDH and exhibits potent and sustained inhibitory action against age-induced apoptosis. N-[3-[N-(4-chlorophenylmethyl)carbamoyl] propanoyl]-L-prolinal inhibits the induction of mRNA of GAPDH to inhibit the expression of GAPDH protein, thereby inhibiting apoptosis.

These facts cannot be explained by the inhibitory action of prolyl endopeptidase (EC3.4.21.26) of N-[3-[N-(4-chlorophenylmethyl)carbamoyl]propanoyl]-L-prolinal and indicate new adaptation. In fact, no variation of PPCE activity is observed in the process of age-induced apoptosis, so that PPCE is not considered to participate in the process. Further, in the age-induced apoptosis of CGC, N-[3-[N-(4-chlorophenylmethyl)carbamoyl]propanoyl]-L-prolinal gave no influence on 30 types or more of surface receptors inclusive of overactivated NMDA receptors.

Pharmacological Activity of the Compound of the Present Invention

N-[3-[N-(4-chlorophenylmethyl)carbamoyl]propanoyl]-L-prolinal has an activity of improving motor dysfunction so that it is useful in the therapy of motor dysfunction caused by, for example, traumas of central or peripheral neurons (spinal cord injuries, spinal cord impact, etc.), infection of central or peripheral neurons, degeneration of central or peripheral neurons (various neurodegenerative diseases, etc.), ischemia in central or peripheral neurons (cerebral ischemia, spinal ischemia, peripheral nerve injuries, etc.) or tumors etc.

As previously described, N-[3-[N-(4-chlorophenylmethyl)carbamoyl]propanoyl]-L-prolinal exhibits GAPDH expression inhibitory action and inhibits age-induced apoptosis. Accordingly, its application to motor dysfunction or neurodegenerative diseases with motor dysfunction is expected. More specifically, it is useful in the therapy of motor dysfunction caused by the apoptosis of neuronal nucleus or paths in cerebellum or spinal cord due to the overexpression of GAPDH, such as Parkinson's disease and Parkinson's symptom, Huntington's disease, Machado-Joseph's disease (MJD), amyotrophic lateral sclerosis (ALS), and Creutzfeld-Jacob's disease (CHJ) etc.

Toxicity

The acute toxicity ($LD_{50}$) of N-[3-[N-(4-chlorophenylmethyl)carbamoyl]propanoyl]-L-prolinal of the present invention was confirmed to be 200 mg/kg body weight in the case of rat by intravenous administration and 2,500 to 5,000 mg/kg body weight in the case of mouse by oral administration. Accordingly, it can be judged that N-[3-[N-(4-chlorophenylmethyl)carbamoyl]propanoyl]-L-prolinal of the present invention is safe enough to be used as a pharmaceutical.

Application to Pharmaceuticals

N-[3-[N-(4-chlorophenylmethyl)carbamoyl]propanoyl]-L-prolinal, nontoxic salts, acid addition salts or hydrates thereof are usually administered systemically or locally, orally or parenterally when used for the above-mentioned purposes.

The dosage, however, depends upon the age, body weight, symptom, therapeutic effect, administering way, treatment time, etc., and normally, oral administration with the dosage ranging between 1 and 1000 mg an adult is made once to a few times a day, or parenteral administration (preferably intravenous administration) with the dosage ranging between 1 and 300 mg an adult is made once to a few times a day, or continuous administration is intravenously made for 1 to 24 hours a day.

As described above, the dosage alters depending upon the various conditions, and therefore, less dosage than the above may be adequate or more may be necessary.

When administering the compounds of the present invention, they are used as internal solid compositions and internal liquid compositions for oral administration and as injections, external preparations, suppositories, etc. for parenteral administration.

The solid compositions for oral administration include tablets, pills, capsules, powders, granules, etc. The capsules include hard capsules and soft ones.

In such solid compositions, one or more active substances are formulated as they are or after mixing them with excipients (lactose, mannitol, glucose, microcrystalline cellulose, starch, etc.), binders (hydroxypropyl cellulose, polyvinyl pyrrolidone and magnesium metasilicate aluminate, etc.), disintegrants (fibrous calcium glycolate, etc.), tablet lubricants (magnesium stearate, etc.), stabilizers, and solution adjuvant (glutamic acid, aspartic acid, etc.) and the like in accordance with the conventional way before they can be used. The tablets and pills may be coated, if necessary, with a coating agent (white sugar, gelatin, hydroxypropylcellulose and hydroxypropylmethylcellulose phthalate, etc.) or two or more films. Additionally, capsules of absorbable substances such as gelatin are also included.

The liquid compositions for oral administration include pharmaceutically acceptable solutions, suspensions, emulsions, syrups, elixirs, etc. In such liquid compositions, one or more active substances are contained in inert diluents generally used (e.g., purified water, ethanol or mixtures thereof, etc.). These liquid compositions may contain moistening agents, suspending agents, emulsifiers, sweetening agents, flavoring agents, antiseptics, buffers, etc.

The injections for parenteral administration include solutions, suspensions and emulsions as well as solids that are dissolved or suspended in solvents when in use. The injections are used after dissolving, suspending or emulsifying one or more active ingredients in a solvent before they can be used. The solvent includes, e.g., distilled water for injection, physiological saline, vegetable oil, and alcohols such as propylene glycol, polyethylene glycol and ethanol, and mixtures thereof. The injections may further contain stabilizers, solution adjuvants (e.g., glutamic acid, aspartic acid, POLYSORBATE 80 (registered trademark), etc.), suspending agents, emulsifiers, soothing agents, buffers, antiseptics, etc. These are sterilized in the final step or prepared by aseptic treatments. These may be prepared as sterile solid compositions and used with dissolving in sterilized or sterile distilled water for injection or other solvents at use.

The other compositions for parenteral administration include external solutions, ointments, endermic liniments, inhalations, sprays, suppositories and pessaries for vaginal administration that contain one or more active substances and are formulated by the conventional methods.

The sprays may contain stabilizers to add stability and isotonicity such as sodium hydrogensulfite, and tonicity agents such as sodium chloride, sodium citrate or citric acid. Methods of preparing sprays are described in detail in, e.g., U.S. Pat. Nos. 2,868,691 and 3,095,355.

BEST MODE FOR CARRYING OUT THE INVENTION

Test Examples

Hereinafter, the motor dysfunction inhibitory action, neuronal cell death inhibitory action and GAPDH expression inhibitory action of N-[3-[N-(4-chlorophenylmethyl)-carbamoyl]propanoyl]-L-prolinal will be described in detail by test examples. However, the present invention should not be construed as being limited thereto.

Test Example 1

Motor dysfunction inhibitory action in spinal cord impact model

Method

A male Wistar rat (about 250 g) was placed in a supine position under anesthesia with sodium pentobarbital (40 mg/kg, i.p.). After partial laminectomy to remove the fifth lumber spine, a silicon rubber (height: 1 mm, length: 4 mm, and width: 1.25 mm) was inserted in the fourth and sixth lumber spines.

After the operation, the maximum walking distance was measured using a treadmill on Day 1, 2, 3, 5, 7 and 14.

That is, the treadmill was run at a speed starting from 10 m/min, with an increment at a rate of 5 m/min every 3 minutes thereafter until the time when the animal dropped from the walking belt and could not walk any further. The walking distance was calculated from the time when the animal could not walk any further.

Results

As shown in Table 1, the maximum walking distance of the vehicle control group significantly decreased as compared with the sham operation group. On the other hand, the group orally administered with 10 mg/kg of N-[3-[N-(4-chlorophenylmethyl)carbamoyl]propanoyl]-L-prolinal (the agent of the present invention) showed a tendency that the maximum walking distance was extended on day 5 (day 2 of administration) and thereafter and on day 14 (day 11 of administration) exhibited a significant improvement of 408±30 m in contrast to 133±93 m by the vehicle control group. On the other hand, the administration of N-[3-[N-(4-chlorophenylmethyl)carbamoyl]propanoyl]-L-prolinal (the agent of the present invention) gave no influence on the autonomic movement and sensitivity to pain.

TABLE 1

| | Maximum Walking Distance (m) | | |
|---|---|---|---|
| | Day 2 after administration | Day 4 after administration | Day 11 after administration |
| Vehicle control | 108 ± 83 | 118 ± 91 | 133 ± 93 |
| Agent of invention (1 mg/Kg) | 237 ± 49 | 414 ± 58 $P < 0.05$ | 347 ± 77 |
| Agent of invention (10 mg/Kg) | 329 ± 15 $P < 0.05$ | 455 ± 34 $p < 0.01$ | 408 ± 30 $p < 0.01$ |

Test Example 2
Motor dysfunction in spinal cord injury

Method

A male Wistar rat (about 250 to 300 g) was subject to dorsal median incision and laminectomy to remove thoracic spine (T11) under anesthesia with sodium pentobarbital and then the dura mater was exposed. A metal pole (diameter: 3 mm, length: 40 mm, weight: 3.8 g) was placed on the dura mater and a load of 10 g was dropped from a height of 10 cm through a cylinder to prepare a crush lesion model. Thereafter, the muscle layer and skin were sutured.

The behavioral deficit was evaluated using modifications of Tarlov scale. That is, the evaluation was made based on mean scores of both hind legs according to the following scores. Neurologic scores:

0 Complete paralysis of hind legs
1 Slight movements of hind legs were observed.
2 Movements of hind legs were clear but the body weight could not be supported so that autonomic movement was impossible.
3 The animal crept and could not support the body weight.
4 The animal could support the body weight when standing or walking. However, clearly disabled.
5 Posture and walking ability are close to those of normal animals.

Results

Figure 1:
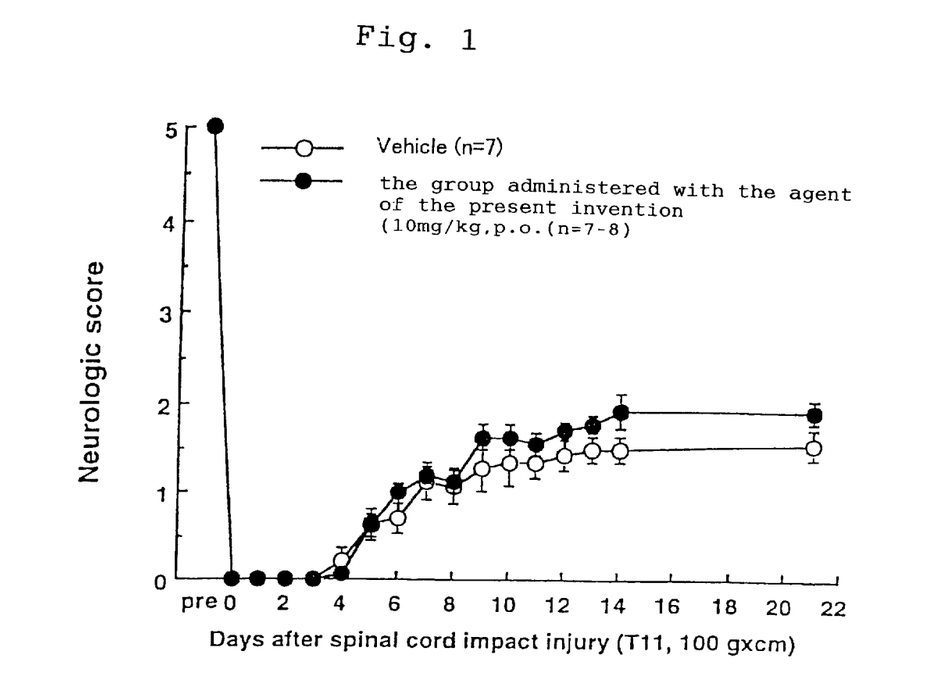
FIG. 1 shows neurologic score of mice of the control group (Vehicle) and of the group administered with N-[3-[N-(4-chlorophenylmethyl)carbamoyl]propanoyl]-L-prolinal (the agent of the present invention) for motor dysfunction in spinal cord injury model.
Figure 2:
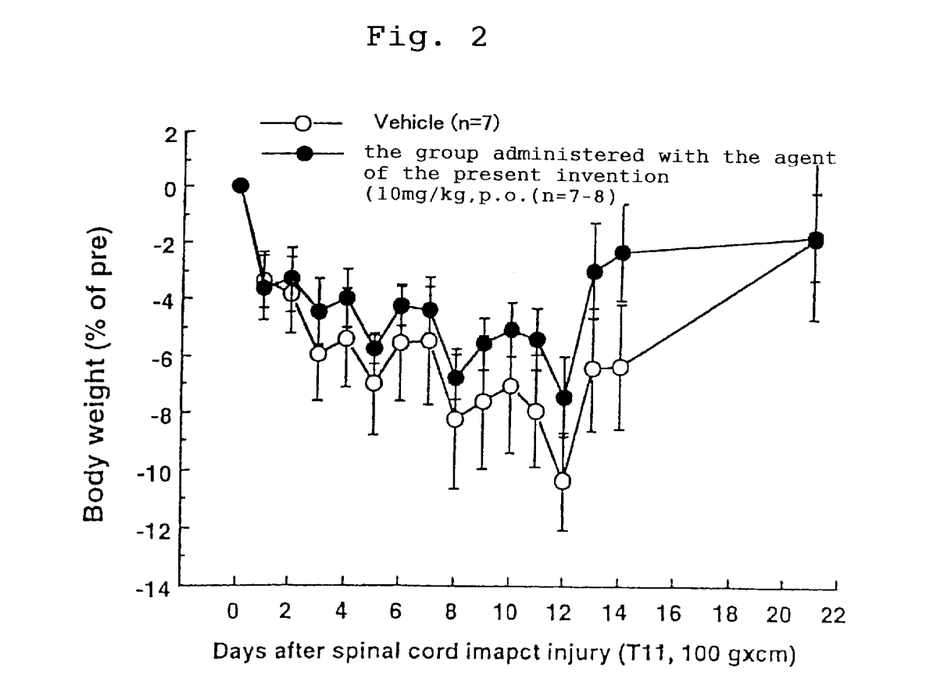
FIG. 2 shows changes In body weight of mice of the control group (Vehicle) and of the group administered with N-[3-[N-(4-chlorophenylmethyl)carbamoyl]propanoyl]-L-prolinal (the agent of the present invention) for motor dysfunction.

Both the vehicle control group ("Vehicle" in FIGS. 1 and 2) and the group administered with N-[3-[N-(4-chlorophenylmethyl)carbamoyl]propanoyl]-L-prolinal (10 mg/kg) ("Agent of Invention" in FIGS. 1 and 2) suffered from complete paralysis of hind legs under score 0 for all cases (15 cases) after awakening from anesthesia and the animals walked with dragging the feet. As of day 4 of the operation, slight recovery of motor dysfunction in any one of the groups and on day 9 of the operation, the degree of recovery for the group administered with N-[3-[N-(4-chlorophenylmethyl)carbamoyl]propanoyl]-L-prolinal tended to be superior as compared with the vehicle control group. This tendency continued up to day 21 of the operation (cf. FIG. 1). Further, with respect to the change in body weight after the operation, the group administered with N-[3-[N-(4-chlorophenylmethyl)carbamoyl]propanoyl]-L-prolinal tended to be superior to the vehicle control group (cf. FIG. 2).

Test Example 3

Age-induced neuronal cell death inhibitory action of N-[3-[N-(4-chlorophenylmethyl)carbamoyl]propanoyl]-L-prolinal Material and Method A) Preparation of primary culture cerebellar granule cells (CGC)

According to the method by Ishitani et al., CGC was prepared as follows (Ishitani et al., J. Neurochem., 66:928–35, 1996).

Cerebellum was excised from an 8-day old Sprague-Dawley rat and cut to 0.4 mm square cubes using McIlawin tissue chopper. Further, the cubes were digested at 37° C. for 15 minutes in a 0.025% trypsin-containing Krebs phosphate buffer (KPB).

After the reaction was stopped with KPB containing 0.008% soybean trypsin inhibitor and 0.0016% deoxyribonuclease I, the digested cubes were triturated in KPB containing 0.01% deoxyribonuclease I and 0.05% soybean trypsin inhibitor using a convergent Pasteur pipette to obtain dispersed CGC.

The cells were suspended in a basal modified Eagle's medium (BME) containing 10% fetal calf serum (FCS), 2 mM glutamine, 50 $\mu$g/ml gentamycin and 25 mM potassium chloride (KCl), and seeded on a plastic dish (35 mm) coated with poly-L-lysine (molecular weight: $3-7\times10^4$, 100 $\mu$g/ml) to a cell density of $2.1\times10^5$ live cells/cm$^2$.

Under 5% carbon dioxide ($CO_2$), culture was started at 37° C. and after 18 to 24 hours cytosine arabinofuranoside (10 $\mu$M) for preventing the growth of non-neuronal cells was added and culture was continued. At 7 DIV (days in vitro), various chemicals were added and thereafter, culture was continued in the same medium.

B) Measurement of viability by live double staining method with FDA-PI

CGC after desired culture days was washed twice with 2 ml of Locke's solution (154 mM NaCl, 5.6 mM KCl, 2.3 mM $CaCl_2$, 1.2 mM $MgSO_4$, 5 mM HEPES, 5.6 mM glucose, 3.6 mM $NaHCO_3$, pH 7.4) and then stained with 0.0008% fluorescein diacetate (FDA) and 0.0002% propidium iodide (PI) for 3 to 5 minutes.

Fluorescent observation was performed using epi-illuminated fluorescent microscope (Olympus, IMT2-RFL) equipped with a dichroic mirror for B excitement (IMT2-DMB), an auxiliary excitation filter (EY455) and an auxiliary filter (O530).

FDA was decomposed by an esterase in the living cells to emit fluorescence (fluorescein) from green to yellow fluorescence, on the other hand PI permeates through dead cell membranes and binds with DNA to emit from red to brown fluorescence, so that the both fluorescences can be observed simultaneously using the above-described fluorescence microscopy.

Viability was calculated according to the following formula.

Viability=[FDA stained cell number/(FDA stained cell number+PI stained cell number)]×100

Results

The primary culture CGC was prepared from 8-day old rat and subcultured in a 25 mM KCl-containing culture medium without exchanging with fresh medium or supplementing glucose.

Figure 3:
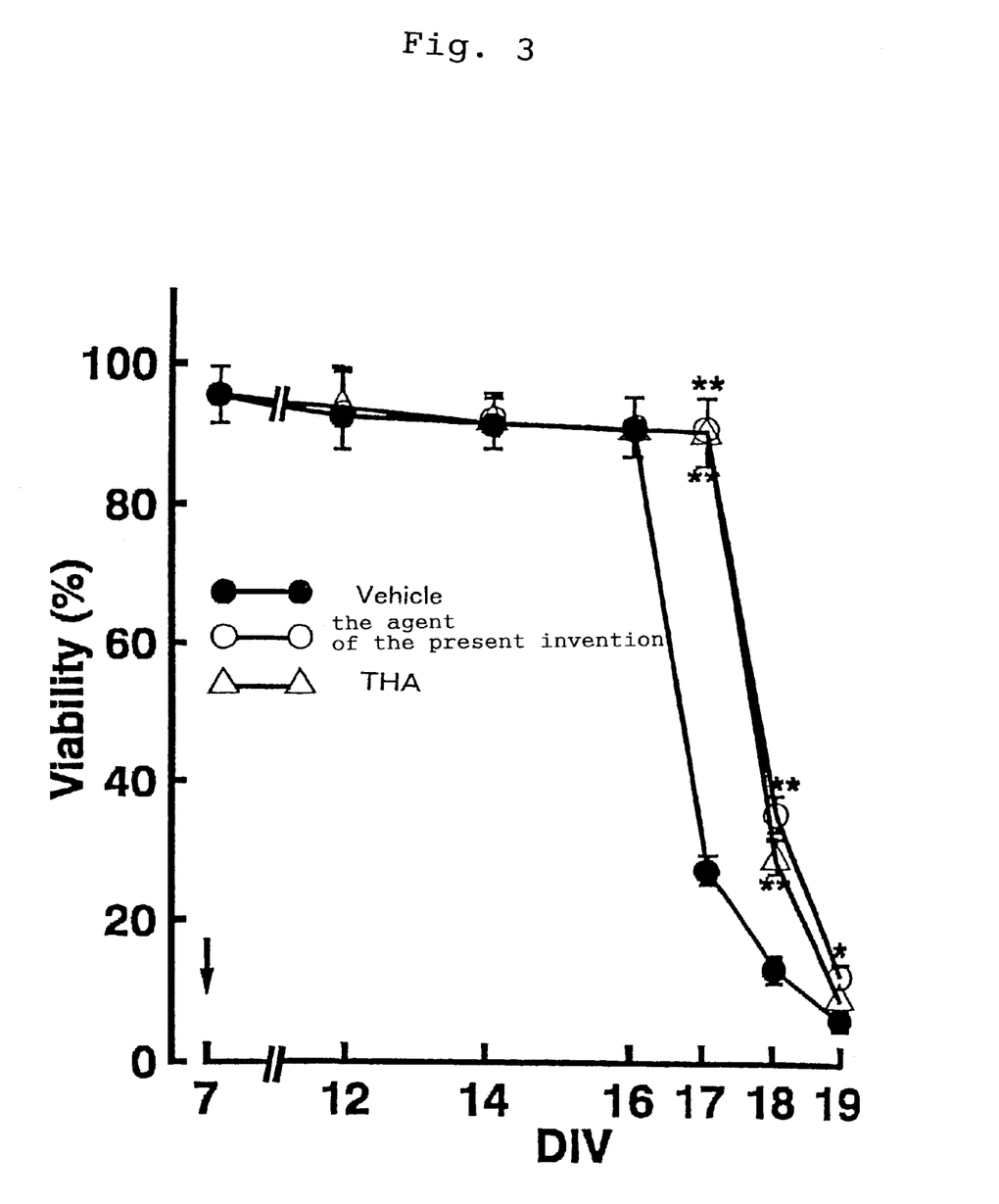
FIG. 3 shows effects with lapse of time on the age-induced apoptosis induced with CGC in the control group, the group administered with the agent of the present invention and the group administered with THA.

As shown in FIG. 3, up to 16 DIV, no cell death was detected but thereafter, abrupt cell death was observed. At 7 DIV, the addition of N-[3-[N-(4-chlorophenylmethyl) carbamoyl]-propanoyl]-L-prolinal (Agent of Invention) (0.03 $\mu$M) significantly retarded the neuronal cell death. That is, the viability of CGC non-treated control group at 17 DIV decreased to 28.5±2.2% while the viability of the group treated with N-[3-[N-(4-chlorophenylmethyl)carbamoyl] propanoyl]-L-prolinal (0.03 $\mu$M) remained to be 92.0±4.4%. That is, age-induced apoptosis was inhibited when the agent of the present invention and THA were added.

In FIG. 3, "Vehicle" represents distilled water and "THA" represents distilled water to which 9-amino-1,2,3,4-tetrahydroacridine (10 $\mu$M) was added.

Figure 4:
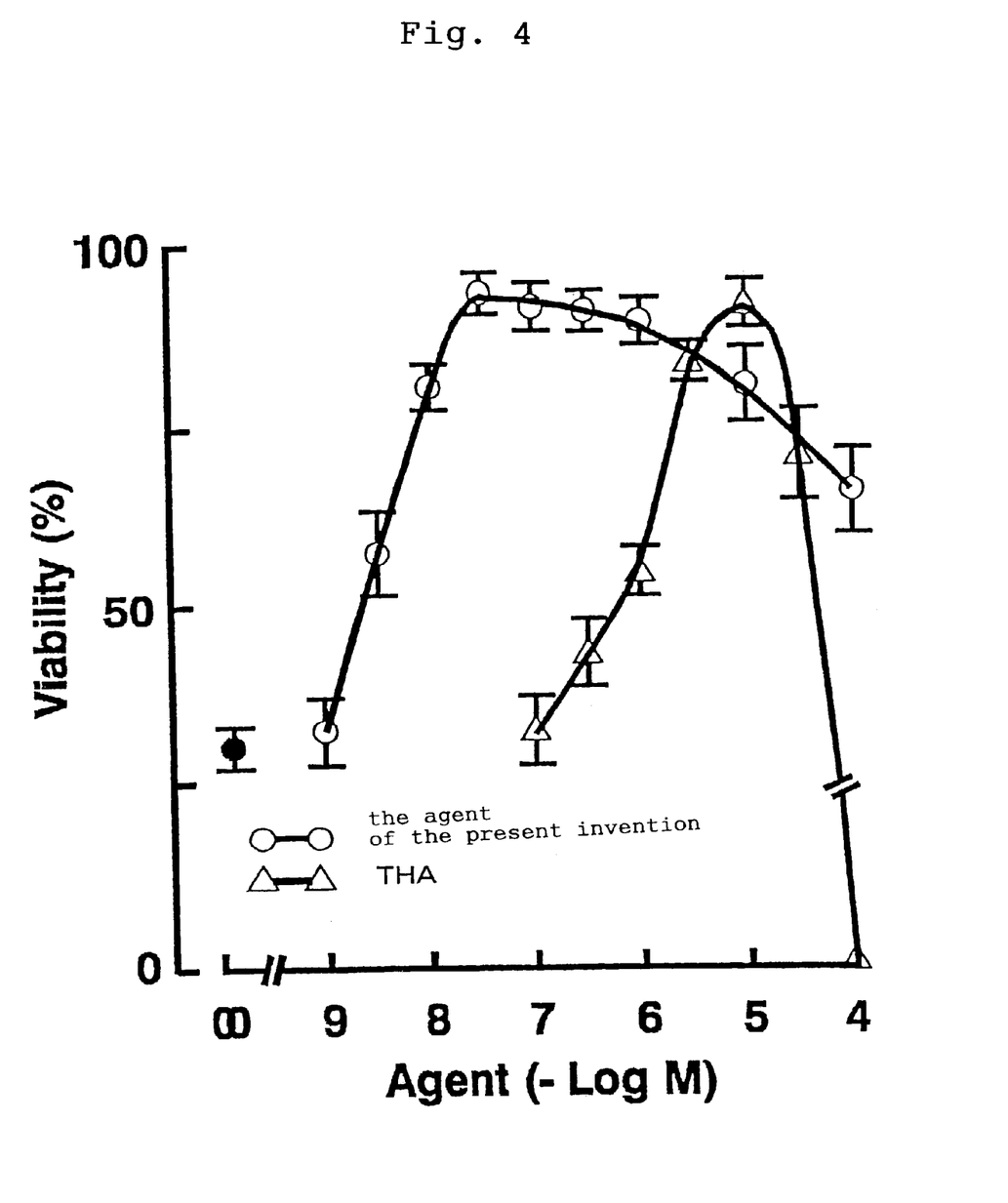
FIG. 4 shows a dose dependence of the agent of the present invention and THA on the age-induced apoptosis induced with CGC.

Further, as shown in FIG. 4, the neuroprotective action of N-[3-[N-(4-chlorophenylmethyl)carbamoyl]propanoyl]-L-prolinal was recognized to be dose-dependent. At 17 DIV, N-[3-[N-(4-chlorophenylmethyl)carbamoyl]propanoyl]-L-prolinal exhibited a protective action to neurons at a concentration of several nM and the maximum action or action close thereto was observed at concentrations between 0.03 to 1 $\mu$M. Thereafter, the action was decreased at concentrations of 10 to 100 $\mu$M. On the other hand, THA inhibited the cell death by about 30% at a concentration of 1 $\mu$M and almost completely at a concentration of 10 $\mu$M, and it exhibited neurotoxicity at a concentration of 100 $\mu$M. Accordingly, the age-induced apoptosis was inhibited over a wide range of concentration by the addition of the agent of the present invention in a dose dependent manner.

Test Example 4

GAPDH mRNA and protein expression inhibitory action of N-[3-[N-(4-chlorophenylmethyl)carbamoyl]propanoyl]-L-prolinal accompanying neuronal cell apoptosis Material and Method A) Northern blotting analysis Preparation of the primary culture cerebellar granule cells (CGC) was performed in accordance with Test Example 3 A).

Then, according to the method of Fukamauchi et al., total RNA was extracted from CGC of the desired culture day number. The total RNA (9 $\mu$g/lane) was electrophoresed on 1.2% agarose formaldehyde gel and transferred to a nylon membrane (Hybond-N, Amersham). Thereafter, it was subjected to prehybridization at 42° C. for 3 to 5 hours in a solution containing 5×Denhardt's solution (0.1% Ficol 400, 0.1% polyvinyl pyrrolidone, 0.1% BSA), 50% formamide, 50 $\mu$g/ml salmon testis DNA, and 0.5% SDS (Fukamauchi et al., J. Neurochem., 56:716–9, 1991, Sunaga et al., Neurosci. Lett., 163:27–30, 1993).

Using a Multi prime DNA labelling kit (Amersham), human GAPDH cDNA probe (Clontech, Palo Alto, Calif., U.S.A.) labeled with [$\alpha$-$^{32}$P] deoxycytidine 5'-triphosphate (3,000 Ci/mm pl) was thermally denatured and thereafter added to the prehybridization solution, followed by hybridization at 42° C. for 24 hours.

The membrane was fully washed at 60° C. for 10 minutes in 0.1% SDS containing 0.1×SSC (35 mM NaCl, 3.5 mM sodium citrate, pH 7.0), exposed on a high-sensitivity X-ray film (IPSO 3000, Fuji) to prepare an autoradiogram. Quantitative analysis was performed using a CCD type image analyzer (BIOPROFIL, M&S).

B) SDS-PAGE and Western blotting analyses

The cultured cells of the desired culture day number were washed three times with 2 ml of PBS and then stripped off by a rubber policeman and the cells were recovered by centrifugation at 188×G at 4° C. for 5 minutes. The cells were resuspended in ice-cooled 50 mM Tris-HCl buffer (pH 7.4) and the cell membranes were destroyed by sonication.

The homogenate was centrifuged at 2×10$^5$×G at 4° C. for 30 minutes to obtain a precipitate (insoluble fraction (pellet)), which was resuspended in the same buffer and then was subjected to quantitative determination of protein together with the supernatant (soluble "supernatant").

According to the Laemmli et al. method, the both fractions were mixed with an equivalent amount of 2×Laemmli sample buffer (20% glycerol, 4% SDS, 10% 2-mercaptoethanol, 0.005% bromophenol blue in 125 mM Tris-HCl, pH 6.8), and thermally denatured at 100° C. for 5 minutes (Laemmli, UK Nature, 227:680–5, 1970).

The same sample was electrophoresed on a linear gradient polyacrylamide gel (manufactured by TEFCO) using Tris-glycine buffer (25mM Tris, 192 mM glycine, and 0.1% SDS) as a running buffer with applying 18 mA rated current.

The gel after the electrophoresis was stained with 0.1% Coomassie blue. The quantitative analysis of the amount of 38-kDa protein band was performed using a CCD type image analyzer (BIOPROFIL, N&S). After performing SDS-PAGE analysis of insoluble fraction proteins, electroblotting on a PVDF membrane (Polyscreen TM, NEN) was performed by the method of Ishitani et al. (Ishitani et al., Mol. Pharmacol., 51:542–50, 1997).

The PDVF membrane after the transcription was treated in 0.5% skim milk containing TBS-T (20 mM Tris, 137 mM NaCl, 0.05% Tween 20, pH 7.4) for 60 minutes to effect blocking, and then was allowed to react at room temperature for 60 minutes in TBS-T containing primary antibody (anti-rabbit GAPDH monoclonal antibody diluted to 1:15000). After washing with TBS-T, similarly the reaction with secondary antibody (peroxidase conjugated rabbit anti-mouse Igs, Dako, Glostrup, Denmark) was performed. After washing the PVDF membrane, quantitative determination of GAPDH protein was performed on a high-sensitivity X-ray film using a detector for chemiluminescence (Renaissance TM, NEN).

Results

1. The present inventors reported that an increase in GAPDH mRNA and accumulation of GAPDH protein in the fraction of membrane participate in the age-induced apoptosis of CGC (Ishitani et al., J. Neurochem., 66:928–35, 1996). Accordingly, as the first stage of elucidating the mechanism of the neuroprotective action of N-[3-[N-(4-chlorophenylmethyl) carbamoyl]propanoyl]-L-prolinal, studies have been made as to whether or not the both pretreated agents give an influence on the increase in GAPDH mRNA in the process of apoptosis and the accumulation of GAPDH protein in the fraction of membrane.

Figure 5:
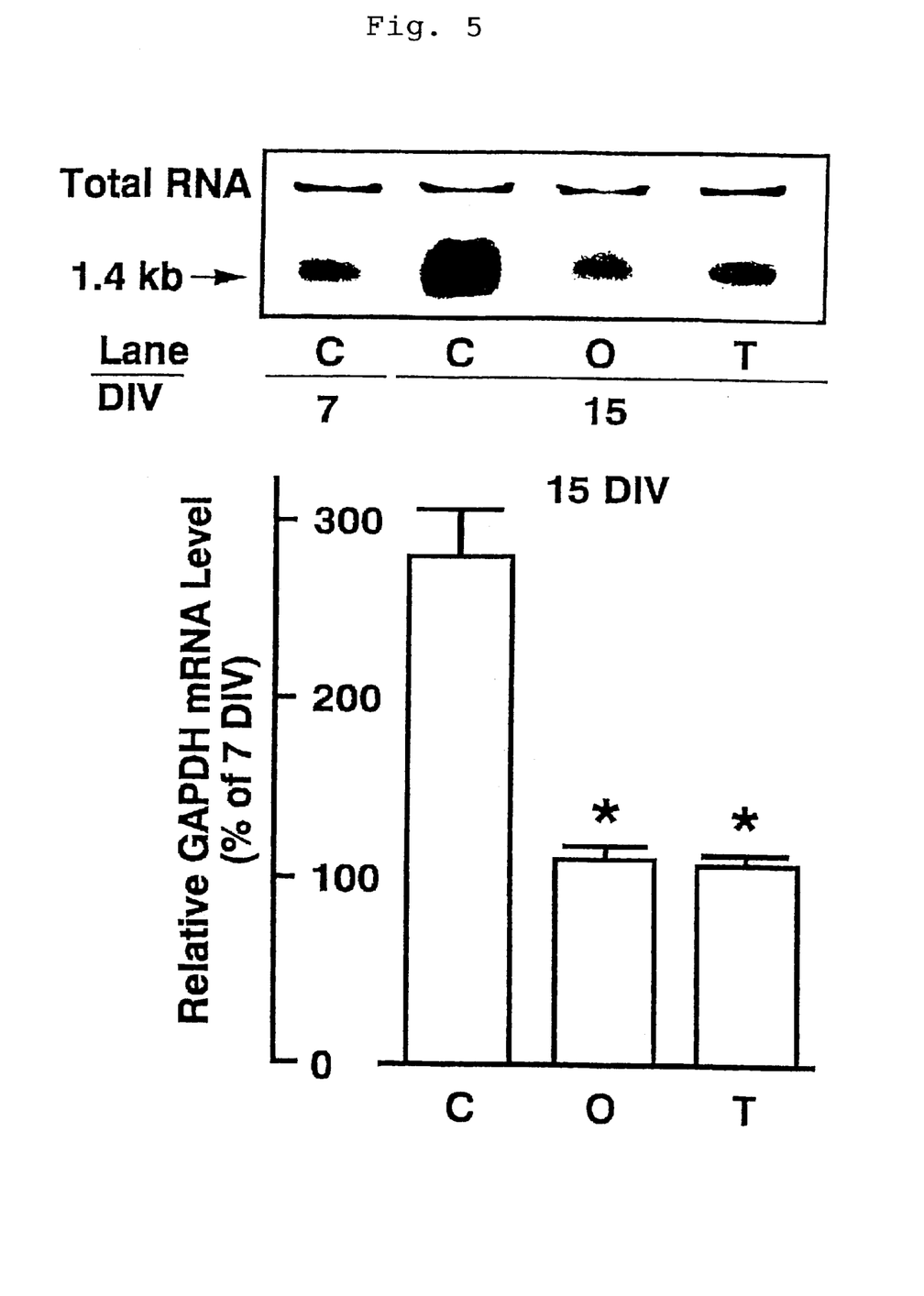
FIG. 5 shows the results of Northern blotting analysis of the effects of the agent of the present invention (O), THA (T) and control (C) on the level of GAPDH mRNA expression that increases prior to the age-induced apoptosis induced with CGC.

As shown in FIG. 5, the addition at 7 DIV of N-[3-[N-(4-chlorophenylmethyl)carbamoyl]propanoyl]-L-prolinal completely inhibited the increase in GAPDH mRNA as much as 2 to 3 times would otherwise be obtained at 15 DIV (CGC). In FIG. 5, "C" represents control, "O" represents Agent of Invention, and "T" represents THA.

Figure 6:
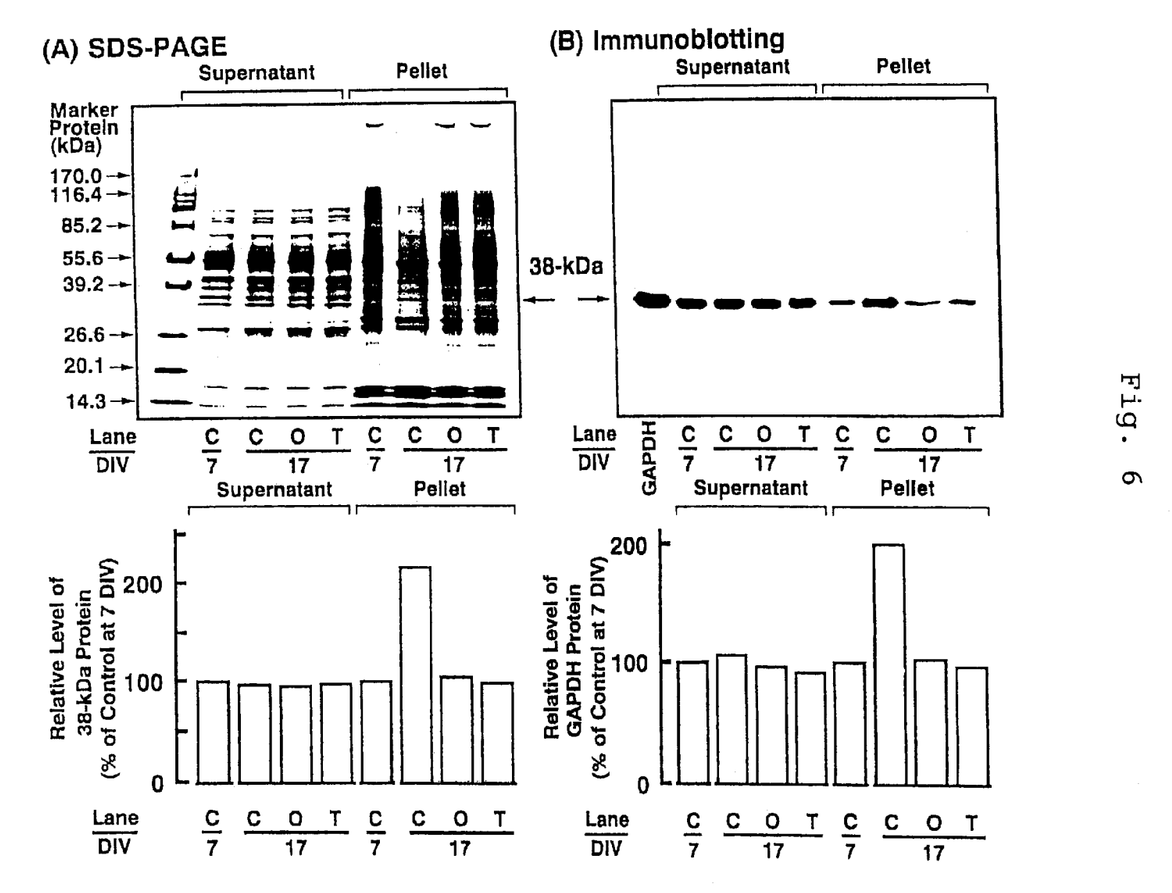
FIG. 6 shows the results of SDS-PAGE (A) and Western blotting (B) analyses of the effects of the agent of the present invention (O), THA (T) and control (C) on the level of GAPDH protein expression that increases prior to the age-induced apoptosis induced with CGC.

2. After performing the centrifugal membrane fractionation of the CGC homogenate and the SDS-PAGE analysis of cell membrane fraction protein, Western blotting analysis was performed. As shown in FIG. 6, as a result of SDS-Page analysis and Western blotting analysis, the level of 38-kDa protein, that is GAPDH, was found to increase about 2 times in the process of age-induced cell death of CGC.

Treatment with N-[3-[N-(4-chlorophenylmethyl)-carbamoyl]propanoyl]-L-prolinal inhibited the increase in the protein. Further, it should be noted that the level of GAPDH in the CGC supernatant fraction did not alter during the process of age-induced cell death and further by the treatment with chemicals (cf. FIG. 6). In FIG. 6, "C" represents control, "O" represents Agent of Invention, and "T" represents THA.

Formulation Example: Production of tablets

The following compounds were mixed by a conventional procedure and tableted to uncoated tablets containing 6 mg of active ingredient per tablet and then coated with hydroxypropylmethylcellulose (HPMC) to obtain 100 film-coated tablets.

| | |
|---|---|
| N-[3-[N-(4-chlorophenylmethyl)carbamoyl]propanoyl]-L-prolinal | 600 g |
| Official lactose | 14.18 g |
| Partially converted α-starch (PCS) | 600 mg |
| Polyhydroxypropylcellulose (HPC) | 300 mg |
| Light anhydrous silicic acid | 40 mg |
| Sodium thiosulfate pentahydrate | 200 mg |
| Magnesium stearate | 80 mg |

What is claimed is:

1. A method for treating motor dysfunction, comprising administering an effective amount of N-[3-[N-(4-chlorophenylmethyl)carbamoyl]propanoyl]-L-prolinal to a patient suffering from motor dysfunction.

2. The method of claim 1, wherein the motor dysfunction is due to a spinal cord injury.

3. The method of claim 1, wherein the motor dysfunction is due to a spinal cord impact.

4. The method of claim 1, wherein the motor dysfunction is due to cerebral ischemia.

5. The method of claim 1, wherein the motor dysfunction is due to a peripheral nerve injury.

6. A method for treating disease due to overexpression of gylceraldehyde 3-phosphate dehydrogenase (GAPDH), comprising administering an effective amount of N-[3-[N-(4-chlorophenylmethyl)carbamoyl]propanoyl]-L-prolinal to a patient exhibiting an overexpression of GAPDH.

7. The method of claim 6, wherein the disease due to overexpression of GAPDH is Parkinsons's disease or Parkinson's syndrome.

8. The method of claim 6, wherein the disease due to overexpression of GADPH is Huntington's disease.

9. The method of claim 6, wherein the disease due to overexpression of GADPH is Machado Joseph's disease.

10. The method of claim 6, wherein the disease due to overexpression of GADPH is amytrophic lateral sclerosis.

11. The method of claim 6, wherein the disease due to overexpression of GADPH is Creutzfeld-Jacob's disease.

12. A method of inhibiting apoptosis, comprising administering an effective amount of N-[3-[N-(4-chlorophenylmethyl)carbamoyl]propanoyl]-L-prolinal to a patient exhibiting apoptosis.

* * * * *

UNITED STATES PATENT AND TRADEMARK OFFICE
CERTIFICATE OF CORRECTION

PATENT NO.    : 6,348,488 B1
DATED         : February 19, 2002
INVENTOR(S)   : Ryoichi Ishitani et al.

It is certified that error appears in the above-identified patent and that said Letters Patent is hereby corrected as shown below:

<u>Title page,</u>
Item [75], the first inventor's residence should read: -- Ryoichi Ishitani, Saitama; Japan --
The second inventor's residence should read: -- Nobuo Katsube; Osaka, Japan --

Signed and Sealed this

Twenty-ninth Day of October, 2002

*Attest:*

JAMES E. ROGAN
*Attesting Officer*    *Director of the United States Patent and Trademark Office*